United States Patent [19]

Solodovnik et al.

[11] Patent Number: 4,999,188

[45] Date of Patent: Mar. 12, 1991

[54] METHODS FOR EMBOLIZATION OF BLOOD VESSELS

[76] Inventors: Valentin D. Solodovnik, ulitsa Novatorov, 36, Korpus 9, kv. 15; Tatyana I. Solodkaya, ulitsa Mikhalkovskaya, 20, kv. 16; Maria T. Litvinova, proezd Kadomtseva, 1, kv. 13; Taisa A. Meshkova, Yaroslavskoe shosse, 120, korpus 2, kv. 157, all of Moscow; Alexandra V. Usova, ulitsa Dzerzhinskogo, 9-A, kv. 55, Kaliningrad Moskovskoi oblasti; Anatoly B. Davydov, ulitsa Krasny Kazanets, 19, korpus 1, kv. 283, Moscow, all of U.S.S.R.

[21] Appl. No.: 362,503

[22] Filed: Jun. 7, 1989

Related U.S. Application Data

[63] Continuation-in-part of Ser. No. 41,646, Apr. 21, 1987, abandoned, which is a continuation of Ser. No. 593,032, Mar. 23, 1984, abandoned.

[30] Foreign Application Priority Data

Jun. 30, 1983 [SU] U.S.S.R. .................... 3613447

[51] Int. Cl.$^5$ .................... A61K 31/74; A61K 49/04
[52] U.S. Cl. .................... 424/78; 424/4
[58] Field of Search .................... 424/4, 78

[56] References Cited

FOREIGN PATENT DOCUMENTS

| 2548902 | 1/1985  | France .              |
|---------|---------|-----------------------|
| 0127322 | 10/1980 | Japan .......... 424/4 |
| 834517  | 5/1960  | United Kingdom .      |
| 886094  | 1/1962  | United Kingdom .      |
| 1174031 | 12/1969 | United Kingdom .      |
| 2014043 | 8/1979  | United Kingdom .      |

OTHER PUBLICATIONS

Kalish et al, The Journal of Urology, vol. 112, pp. 138–141.
Soimakallio et al, Annales Chirugiae et Gynaecologiae 70:112–115, 1981.
Kato et al, Cancer, Aug. 1, 1981, vol. 48, 674–680.

*Primary Examiner*—Stanley J. Friedman
*Assistant Examiner*—Raymond J. Henley, III
*Attorney, Agent, or Firm*—Ladas & Parry

[57] ABSTRACT

A composition for embolization of blood vessels contains the following ingredients in weight percent:

| particles of an embolizing material | from 0.01 to 15.0 |
|-------------------------------------|-------------------|
| polyalkyleneoxide                   | from 0.02 to 0.2  |
| fluid medium                        | the balance.      |

The composition can be used in surgery for reducing blood supply of individual organs, preventing haemorrhage, producing ischemia of malignant tumors and many other cases.

2 Claims, No Drawings

METHODS FOR EMBOLIZATION OF BLOOD VESSELS

This is a continuation-in-part of copending application(s) Ser. No. 07/041,646 filed on Apr. 21, 1987 now abandoned which is a continuation of co-pending application Ser. No. 06/593,032 filed on Mar. 23, 1984 (now abandoned).

FIELD OF THE INVENTION

This invention relates to medicine and, in particular, to a composition for embolization of blood vessels, which can be used in surgery to reduce the blood supply of individual organs or parts thereof in order to prevent hemorrhages caused by trauma or from esophageal and gastric veins hypervascularized by portal hypertension, or to induce ischemia of malignant tumors, and in many other cases.

BACKGROUND ART

Known in the art is arterial embolization by coarse dispersions of autologous clots, subcutaneous fat, muscle etc. (cf., for example, M. Kalish, L. Greenbaum, S. Silber, H. Goldstein: Traumatic Renal Hemorrhage Treatment by Arterial Embolization. The Journal of Urology, 1974, Vol. 112, No.1, p.138).

Such emboli can, even if thrombin is injected, make only temporary occlusions lasting from several hours to several days, since they are subjected to lysis, the vessel is prematurely recanalized and hemorrhage recurs. Moreover, such compositions can contain radiopaque and physiologically active substances only in the fluid used for dispersion of embolizing particles. The embolizing material cannot be strictly controlled and the prolonged action of physiologically active substances cannot be controlled at the site of emboli.

Also known in the art are compositions for arterial embolization, containing exogeneous materials, such as particles of natural or synthetic polymers, glass, metals in combination with water or physiological solutions (cf., S. Soimakallio, J. Lahtinen, S. Tanska: Arterial Embolisation in the Treatment of Malignant Tumours, Annales Chirurgiae et Gynaecologiae, 1981, Vo. 70, No. 3, p.112). These compositions contain irregularly shaped and sized particles and cannot ensure reliable embolization of vessels.

There are known compositions for embolization of blood vessels, containing water or a physiological solution and polymer particles of a specific size, either close to, or less than, the diameter of the catheter, which comprise a nonpolarpolymer (ethylcellulose, for example) as the basic particle material and a physiologically active preparation, mitomycin C, for example, which is released from the particles at a slow rate due to the low polarity of the polymer (cf., T. Kato, R. Nemoto et al, Cancer, 1981, V.48, No.3, pp.674–680).

However, it is not easy at all to introduce particles of the above composition into a blood vessel through a catheter because of friction and deceleration of the particles which agglomerate in the catheter and finally block it since its diameter exceed the particle diameter by a factor of two or three at the most. In consequence, such compositions can only be infused into a vessel in limited amounts, carrying a limited number of particles until the catheter is clogged. This small number of particles (emboli) can be only introduced with a large amount of the physiological solution. Thus, when the size of the emboli is 225 micrometers they can be infused as a dispersion in a dose of 10–75 mg at the most in 20 milliliters at the least of the physiological solution. This produces an extra load of the ballast solution on the blood vessel and, in addition, an embolus can stray into lateral vessels.

SUMMARY OF THE INVENTION

The primary object of the invention is to provide a composition for embolization of blood vessels, in which agglomeration of particles is decreased as the composition is introduced.

Another object of the invention is to provide a composition which, when physiologically active substances are added thereto, can prolong the action of said substances.

These and other objects are achieved in that the composition for embolization of blood vessels comprising particles of an embolizing material and a fluid medium also comprises, according to the invention, polyalkyleneoxide of a molecular weight such that the composition does not clog a catheter or syringe, the initial ingredients being in the following ratio on the weight percentage basis:

| | |
|---|---|
| particles of an embolizing material | from 0.01 to 15.0 |
| polyalkyleneoxide | from 0.02 to 0.2 |
| fluid medium | the balance. |

The proposed composition can additionally comprise a medicinal or radiopaque substance or a mixture of these in an amount of about 0.005 to about 8% by weight in relation to the total weight of the initial ingredients. The proposed composition preferably comprises polymethyleneoxide, polyethyleneoxide or polypropyleneoxide as polyalkyleneoxide. The proposed composition comprises, as particles of the embolizing material, particles of a polymer material moderately swelling in water, particles of glass or metal or a mixture thereof.

The proposed composition preferably comprises, as particles of the polymeric material, particles of acetylcellulose, acetylphtalylcellulose, polyvinylacetate, copolymers of vinylpyrrolidone and methylmethacrylate.

The proposed composition preferably comprises, as the fluid medium, water solutions of sodium chloride or glucose.

The composition, according to the invention, contains polyalkyleneoxide, and because of this embolizing particles have no difficulty in going through the catheter in required doses, less liquid is needed to infuse embolizing particles, these particles can be supplied to arteries located far from the point where the catheter is introduced, which means a much longer catheter can be used, and no special treatment of the catheter internal surface is required.

DETAILED DESCRIPTION OF THE INVENTION

The weight ratio of the ingredients of the proposed composition for embolization of blood vessels is conditioned by the fact that, when the share of the embolizing material in the composition is less than 0.01%, too much liquid is injected into the artery and the danger of emboli straying into lateral vessels becomes so real one cannot ignore the consequences of embolization of vital organs and tissues. When the share of the embolizing material in the composition is more than 15%, the catheter or the needle can be easily clogged.

If the amount of polyalkyleneoxide goes below 0.02%, the primary advantage of the proposed composition is substantially affected, this advantage being the ability of the particles to go through the catheter freely with a comparatively small amount of the fluid medium. If, on the other hand, the content of polyalkyleneoxide goes above 0.2%, the physical and mechanical properties of the embolizing particles contained in the fluid medium can be seriously effected—they become fragile, polyalkyleneoxide is washed into the fluid medium or, when the embolizing material contains some physiologically active substance, this substance is easily transported from the particles into the fluid medium or to blood and the effect of prolonged action is weakened.

If the amount of the radiopaque substance in the preparation goes below 0.005% by weight, the particles become difficult to monitor in the process of embolization. If, on the other hand, the amount of a radiopaque substance rises over 8% by weight, the composition becomes less mobile, its apparent viscosity rises, the physical and mechanical properties of the particles deteriorate. The composition turns more dense and difficult to handle during infusion.

The proposed composition is prepared by known methods. Polyalkyleneoxide can be either a part of the fluid medium or of the particles of the embolizing material. The latter can be achieved in the process of making embolizing material particles by mixing polyalkyleneoxide with the material of embolizing particles before they are formed.

The safety and efficiency of the proposed composition for embolization of blood vessels were tested in the course of systematic medical and biological assays on animals, toxicological analyses for acute and systemic toxicity, histological studies and functional examinations, and clinical evaluation on patients having a variety of indications for embolization. The composition for embolization of blood vessels contained polyethyleneoxide as polyalkyleneoxide, various physiologically active substances, such as trihydrate of 6-[D(—)a-aminophenilacetamido]-penicillinic acid (ampiox) or cyclophosphane, radiopaque substances, such as $Fe_2O_3$ $6BaO$ (barium ferrite) or tantalum, polymeric materials, such as acetylcellulose or a copolymer of N-vinylpyrrolidone-2 and methylmethacrylate, which swells moderately in water, or acetylcellulose. Hemolytic effects of the proposed compound were tested in vitro using extracts from samples of said composition. It was definitely shown they have no hemolytic effect.

Acute and chronic experiments on rabbits and dogs, lasting for 30 days after infusion, demonstrated that the proposed composition for embolization can be infused, in doses excedding those without polyalkyleneoxide by a factor of from 2 to 4, into blood vessels using conventional catheters with an internal diameter of 1 mm and up to 50 cm long, so that medium and even small caliber vessels could be embolized.

Thirty days of observation of animals have positively demonstrated that the proposed composition is functionally suitable for embolization, the ingredients contained therein are not toxic even when released for prolonged periods, the target vessels are reliably embolized for long periods. The pronounced embolizing effect was registered in all cases. No test animal died from causes connected with the infusion of the proposed composition.

Visual observation in the post-infusion period registered ischemia of tissue (of the leg) when microemboli were introduced into the femoral artery without any indications of suppuration.

Morphological tests performed in 7 days after embolization demonstrated that the vessel lumen was blocked by an unorganized thrombus tightly held against the endothelium of the internal vascular layer. The external arterial layer seemed without visible changes.

On the 14th day after embolization an organized thrombus was observed in the vessel lumen to be intimately adherent to the vessel wall. Clots of fibrin were interspersed with spaces containing emboli. The spaces were lined with epithelioid cells while the periphery of the thrombus had already shown signs of revascularization. The vascular content was composed of erythrocytes, neutrophilic leukocytes, single lymphocytes and cellular detritus. The external vascular wall and adjoining tissue seemed without changes.

Preliminary test results have confirmed that the compositions were not histotoxic and could be used for embolization of blood vessels. They were found much more convenient to handle when infusing through catheters as compared to compositions without polyalkyleneoxide.

Local chemotherapy by the proposed composition containing cyclophosphane in addition to polyethyleneoxide was also tested for efficiency in conditions of ischemization of a tumoured organ.

Four series of tests were conducted using 98 male rats with transplanted Walker carcinosarcoma. The weight of animals ranged from 180 to 190 g. The tumor was initiated by injecting 0.4 ml of 25% tumor tissue suspension with a 0.9% sodium chloride solution into the right gastrocnemius muscle. The primary indications of the effect of the tested technique on the tumor growth were the changes in the tumor volume and the survival period.

The target of the first series of tests was the effect of the local ischemia on the tumor growth. The animals were broken into two equal groups. In one group branches of the femoral artery feeding the tumor were separated and ligated in 5 days after the tumor transplantation, since infusion of emboli into very narrow blood vessels of a rat was not technically possible. In the second group the animals were left as they were (reference group) after transplantation. The results of this experiment are shown in Table 1.

Tumor reduction started on the next day after ligation of the blood vessels and went on for 4 to 6 days. The subsequent acceleration in the tumor growth was evidently connected with vascularization of the collateral blood vessels and restoration of circulation in the tumor area. The survival period of experimental animals in the first group was much longer (by 28.1%). It can be concluded that interruption of the tumor blood supply results in reduction of its growth and longer survival period of experimental animals.

The second series of tests was to find out the effect of the chemotherapy in conditions of tumor ischemia. Experimental evidence of the chemotherapy in ischemic conditions is still insufficient and no proof exists that drug transportation to the tumor area is not slowed down by limitation of the tumor blood supply.

The experimental animals were divided into four groups. In the first group, branches of the femoral arteries were ligated in 5 days after tumor transplantation and cyclophosphane was introduced once directly to the tumor tissue in a dose of 0.06 g/kg of the animal weight. In the second group, cyclophosphane was introduced at the same time and in the same amount but no blood vessels were ligated prior to that. In the third group, blood vessels were ligated but no drugs administered. The fourth was the reference group. The results of the experiments are shown in Table 2.

Referring to Table 2, ligation of the arterial vessels supplying the tumor and introduction of cyclophosphane into the tumor result in marked reduction of the tumor growth as contrasted to the reference group. Since the preparation is released into the general blood flow in lesser amounts, it means a higher concentration of the preparation at the tumor site. A more pronounced initial tumor-reducing effect of cyclophosphane in the second group is, evidently, due to its fast arrival to the tumor cells followed by subsequent fast removal to the general blood flow. The concentration drops sharply, and in 5 or 6 days after the introduction of the preparation the tumors in this group are already larger than in the first group. The tumor-reducing effect of vessel ligation in the third group was the lowest as contrasted to the two groups where cyclophosphane was used. The lifetime of the experimental animals in the first group, as compared to the second and third groups, increases by 20.1% and 42.9%, respectively, and by 100% as opposed to the animals in the reference group.

The third series of tests was to study the use of the proposed composition which contains particles of acetylcellulose and cyclophosphane as the embolizing material particles.

Experimental animals were divided into four groups. Those in the first group received, in 5 days after tumor transplantation, an intraperitoneal infusion of a composition wherein emboli with a particle size of from 100 to 140 micrometers contained cyclophosphane (12.5% per emboli weight) rated at 0.12 g per kg of animal weight. A composition without cyclophosphane was introduced to the animals in the second group in the similar manner. A single infusion of cyclophosphane in an amount of 0.12 g per kg of animal weight was given to the animals in the third group. The fourth was the reference group. The results of the tests are shown in Table 3.

Referring to the Table 3, the tumor-reducing effect in the first group became evident later than in the group where only cyclophosphane was infused, which can be attributed to the gradual release of cytostatic from the emboli having the composition according to the invention. In the second group the dynamics of changes in the tumor size and the survival period of experimental animals were almost no different from those in the reference group. Intraperitoneal infusion of cyclophosphane resulted in fast reduction of the tumor growth rate and subsequent acceleration of the growth rate, which is usually explained by rapid entry of the preparation into the general blood flow and its equally rapid disappearance. Hypodynamia and diarrhea of the animals in this group were clearly manifestations of the toxic properties of cyclophosphane. Such toxic effects in the first group were not readily noticeable. The lifetime of animals in the first group is by 15.8% and 68.3% longer than of those in the third and fourth groups, respectively.

In order to produce a model representative, to a sufficient degree of the conditions of chemoembolization of tumor blood vessels, the arterial vessels supplying the tumor were ligated and the proposed composition containing cyclophosphane was administered by puncture to the tumor. The experiment involved four groups of animals. The animals of the first group were infused, in 5 days after tumor transplantation, with a composition containing cyclophosphane in emboli in an amount of 0.12 g of cyclophosphane per 1 kg of the body weight. Prior to infusion, branches of the femoral artery supplying the tumor were ligated. In the second group compositions containing polyethyleneoxide and cyclophosphane were infused in the similar manner in the same dose, but arteries were not ligated. The third group of animals had their arteries ligated. The fourth group was the reference group. The results of the experiment are shown in Table 4.

The data obtained in this experiment clearly show that the tumor growth rate reduction and lifetime figures are better in the first group, which can be attributed to the combination of the effects of the ischemia and cyclophosphane on the tumor, when the composition according to the invention is introduced. As contrasted to the reference group, the survival period is 118.7 percent longer in the first group.

The experiments have shown that the proposed composition provides a stable and sufficiently high concentration of the preparation at the tumor site so that a longer contact of the preparation with tumor cells is ensured. In addition, the use of the proposed composition provided for ischemization of the tumor, resulting in a combined effect of ischemization and local chemotherapy.

In another experiment, four dogs were used for embolization of the splenic artery by the proposed composition containing 40% of microemboli made of acetylcellulose with a diameter of from 0.3 to 0.5 mm and from 0.5 to 0.7 mm, polyethyleneoxide (0.02%) and water in order to find out if it is possible to produce ischemia of the spleen during hypersplenism. The composition was infused through a 1 mm polyvinylchloride catheter into arteries. Experimental animals were under observation for as long as 6 or 14 days.

Histological tests have uncovered development of focal hemorrhagic infarctions in the spleen followed by scarring. No suppuration areas were found. Microemboli could be seen in the lumens of large (up to 1 mm) blood vessels. They were closely adhesioned with internal vessel walls, which testifies to the reliability of embolization. No control experiment, where compositions without polyethyleneoxide were used, could produce embolization because the catheter was clogged by the emboli.

In clinical conditions, six patients with hypoplastic anemia were subjected to embolization of the splenic artery with positive clinical effect. The embolization composition contained 0.3–0.5 mm emboli made of acetylcellulose, ampiox, polyethyleneoxide and tantalum.

Clinical assays have demonstrated that the proposed compositions can be easily infused into a blood vessel in a required dose, produce reliable embolization, and can be roentgenologically monitored as they are infused into the arterial channel and as the artery occlusion develops.

For better understanding of the present invention several examples of concrete embodiments of the proposed composition and methods fo their preparation are given below.

EXAMPLE 1

A composition for embolization of blood vessels, containing the following ingredients:

| | |
|---|---|
| spherical particles of embolizing material made of acetylcellulose substitution degree - 2.4 to 2.5; content of acetyl groups 38 to 40%; viscosity of a 5% solution in acetone - 0.07 Pa. sec., and polymerization degree - 150–160, diameter 0.2–0.3 mm, | 0.80 g |
| polyethyleneoxide, molecular weight - 400 and polymerization degree - 8.6 to 8.7. | 0.001 g |
| water | 5 ml. |

A 0.02% water solution of polyethyleneoxide is prepared in advance. A batch of spherical acetylcellulose particles with a diameter of from 0.2 to 0.3 mm is added to 5 ml of the above solution. The composition is drawn into a syringe which is connected with a polyvinylchloride catheter with an internal diameter of 1 mm and 200 mm long and infused at a rate of 10 to 20 ml/min.

This composition passes through the catheter without difficulty. Similar results are obtained by using acetylcellulose having a substitution degree of 2.1 to 2.3, content of acetyl groups of 36 to 37.9%, and polymerization degree of 165 to 600, and by using polyethyleneoxide having a molecular weight of 600, 1,000, 2,000, 6,000, and 200,000.

To prepare spherical particles of embolizing material from acetylcellulose (USSR Inventor's Certificate No. 485,759), 0.1 liter of 3 to 5% solution of acetylcellulose in acetone is emulsified by agitation with an anchor mixer at a rotation speed of 2 to 10 sec$^{-1}$ in 0.3 to 0.5 liter vaseline oil at 15° to 25° C., as air is passed through the mixture at a rate of 50 to 100 ml/sec at constant agitation. After the particles have solidified they are filtered off, washed with hexane, dried and fractionated according to size using sieves with a mesh size of 200 to 300 μm.

EXAMPLE 2

A composition for embolization of blood vessels, containing the following ingredients:

| | |
|---|---|
| Spherical particles of embolizing material made of acetylphtalylcellulose, substitution degree - 2.1 to 2.5, polymerization degree - 100 to 500, and the content of phthalyl groups of 20 to 40%, and of acetyl groups - 20 to 40%, diameter: 0.2–0.3 mm | 0.89 g |
| polymethyleneoxide, molecular weight of 300 to 400, and polymerization degree of 10 to 13. | 0.01 g |
| water | 5 ml. |

A batch of spherical particles of the embolizing material made of acetylphtalylcellulose is added to 5 ml of 0.2% water solution of polymethyleneoxide. The composition is drawn into a syringe which is connected to a polyvinylchloride catheter having an internal diameter of 1 mm and 200 mm long and infused at a rate of 10 to 20 ml/min.

This composition passes through the catheter without difficulty.

EXAMPLE 3

A composition for embolization of blood vessels, containing the following ingredients:

| | |
|---|---|
| Spherical particles of embolizing material made of acetylcellulose and containing 50% of ampiox, diameter: from 0.2 to 0.3 mm | 0.6 g |
| polyethyleneoxide | 0.011 g |
| water | 5 ml. |

A composition is further prepared as in Example 1, using a 0.22% solution of polyethyleneoxide in water. This composition passes through the catheter described in Example 1 without difficulty.

EXAMPLE 4

A composition for embolization of blood vessels, containing the following ingredients:

| | |
|---|---|
| spherical particles of embolizing material made of polyvinylacetate, molecular weight of 20,000, viscosity of the solution of 86 g of polymer in 1 liter of benzene at 20° C. of 3cP, and softening point, 35 to 45° C., diameter: from 0.2 to 0.3 mm | 0.20 g |
| polypropyleneoxide, molecular weight of 4,000 (Polypropylene glycol 4000, Serva Feinbiochemica GMBH and Co., BRD) | 0.01 g |
| water | 5 ml. |

A 0.2% water solution of polypropyleneoxide is prepared. The composition is further prepared as in Example 1. The composition passes without difficulty through the catheter whose dimensions are indicated in Example 1.

Similar results are obtained by using polyvinylacetate having a molecular weight of 40,000 to 160,000 and polypropyleneoxide having a molecular weight of 800, 2,000 and 10,000.

EXAMPLE 5

A composition for embolization of blood vessels, containing the following ingredients:

| | |
|---|---|
| Spherical particles of embolizing material made of acetylcellulose and containing 50% of barium ferrite and 0.4% of polyethyleneoxide | 0.60 g |
| 0.9% sodium chloride solution | 5 ml. |

Spherical particles are obtained as in Example 1, by adding barium ferrite and polyethyleneoxide in desired proportions to the solution of acetylcellulose in acetone. To obtain the proposed composition a batch of said spherical particles with a diameter of from 0.2 to 0.3 mm is added to 5 ml of the 0.9 water solution of sodium chloride. This composition is drawn into a syringe connected to a polyvinylchloride catheter with an internal diameter of 1 mm and 200 mm long and infused at a rate of 10 to 20 ml/min.

The composition passes without difficulty through the catheter.

EXAMPLE 6

A composition for embolization of blood vessels containing the following ingredients:

| | |
|---|---|
| spherical particles of embolizing material made of a copolymer of vinylpyrrolidone and methylmethacrylate, containing 50% tantalum powder and 0.02% polyethyleneoxide | 0.6 g |
| 5% water solution of glucose | 5 ml. |

Spherical particles of embolizing material are obtained as in Example 5, using a copolymer of N-vinylpyrrolidone-2 and methylmethacrylate, at a molar ratio of the units of 10-40:90-60, molecular weight of 5,000 to 500,000, with a statistical arrangement of the comonomer units, prepared in the presence of free radical polymerization initiators, and a tantalum powder with a particle size of 0.5 to 10 m, in place of barium ferrite.

To obtain the composition, a batch of said spherical particles with a diameter of from 0.2 to 0.3 mm is added to 5 ml of the 5% water solution of glucose. This composition passes without difficulty through the polyvinylchloride catheter with an internal diameter of 1 mm and 200 mm long.

EXAMPLE 7

A composition for embolization of blood vessels containing the following ingredients:

| | |
|---|---|
| spherical particles of embolizing material made of acetylcellulose, with a diameter of from 0.2 to 0.3 mm, containing 0.1% thiophosphamide and 0.4% polyethyleneoxide | 0.6 g |
| water | 5 ml |

Spherical particles are obtained as in Example 5, using thiophosphamide in place of barium ferrite. This composition passes without difficulty through the catheter whose dimensions are indicated in Example 2. A composition is further prepared by mixing the ingredients.

EXAMPLE 8

A composition for embolization of blood vessels, containing the following ingredients:

| | |
|---|---|
| spherical particles of embolizing material containing 80% tantalum powder and 20% acetylcellulose having a diameter of 0.3 to 0.5 mm | 0.56 g |
| polyethyleneoxide | 0.01 g |
| water | 5 ml. |

Spherical particles are obtained as in Example 1 by adding tantalum powder, with a particle size of 0.5 to 10 μm, to the solution of acetylcellulose in acetone. A 0.02% water solution of polyethyleneoxide is prepared. The composition is further prepared as in Example 2.

This composition passes without difficulty through the catheter whose size is indicated in Example 2.

EXAMPLE 9

A composition for embolization of blood vessels, containing the following ingredients:

| | |
|---|---|
| spherical particles of embolizing material made of glass with a diameter of from 0.2 to 0.3 mm | 0.8 g |
| polyethyleneoxide | 0.001 g |
| water | 5 ml. |

The composition is prepared as in Example 1. It passes without difficulty through the catheter whose size is indicated in Example 2.

EXAMPLE 10 (REFERENCE)

A composition for embolization of blood vessels, containing the following ingredients:

| | |
|---|---|
| spherical particles of embolizing material made of acetylcellulose with a diameter of from 0.2 to 0.3 mm | 0.3 g |
| water | 5 ml. |

A batch of said spherical particles is added to 5 ml of water. The composition is drawn into a syringe which is connected to a catheter made of polyvinylchloride with an internal diameter of 1 mm and is 200 mm long and infused at a rate of 10-20 ml/min. The bulk of the composition remains in the syringe since the particles clog the catheter.

EXAMPLE 11 (REFERENCE)

A composition for embolization of blood vessels, containing the following ingredients:

| | |
|---|---|
| spherical particles of embolizing material made of polyvinylacetate with a diameter of from 0.2 to 0.3 mm | 0.2 g |
| water | 5 ml. |

The composition is prepared as in Example 10. This composition also clogs the catheter of the size indicated in Example 2.

EXAMPLE 12 (REFERENCE)

A composition for embolization of blood vessels, containing the following ingredients:

| | |
|---|---|
| spherical particles made of a copolymer of vinylpyrrodoline and methylmethacrylate, containing 25% ampiox and 25% barium ferrite with a diameter of 0.2 to 0.3 mm | 0.2 g |
| water | 5 ml. |

The composition is obtained as in Example 10. This composition also clogs the catheter of the size indicated in Example 2.

EXAMPLE 13 (REFERENCE)

A composition for embolization of blood vessels, containing the following ingredients:

| | |
|---|---|
| spherical particles made of acetylcellulose as in Example 1, diameter of 0.2 to 0.3 mm | 0.30 g |
| Ethylene glycol, MP −10° | 0.011 g |
| water | 5 ml. |

A 0.22% water solution of ethylene glycol is prepared in advance. A composition as in Example 1 is further prepared and used. The bulk of the composition remains in the syringe since the particles clog the catheter.

The same result is obtained when diethylene glycol instead of ethylene glycol is used.

EXAMPLE 14 (REFERENCE)

A composition containing the following ingredients:

| | |
|---|---|
| spherical particles as in Example 1 | 0.3 g |
| 3% aqueous solution of partially hydrolyzed dextran with a molecular weight of 30,000 to 40,000 (polyglucine) | 5 ml |

The composition is used as in Example 1 to obtain a result similar to the result obtained in Example 10.

EXAMPLE 15

A composition for embolization of blood vessels containing the following ingredients:

| | |
|---|---|
| spherical particles of embolizing material from acetylcellulose, obtained as described in Example 1, diameter 0.5 to 0.7 mm polyethyleneoxide of molecular weight of 200,000 (Polyethylene Glycol 200000 pract., polymerization degree 4,500, Serva Feinbiochemica GMBH and Co., BRD), and m.p. 60–65° | 0.010 g |
| water | 5 ml. |

The composition is prepared by mixing spherical particles of embolizing material with 5 ml of 0.2% solution of polyethyleneoxide in water and is used in Example 1. The result is similar to that obtained in Examples 1 to 9.

EXAMPLE 16

A composition for embolization of blood vessels containing the following ingredients:

| | |
|---|---|
| spherical particles of embolizing material from ethylcellulose obtained as described in Example 5, comprising 25% cyclophosphane and 0.2% polyethyleneoxide, diameter 0.2 to 0.3 mm | 0.8 g |
| water | 5 ml. |

To obtain spherical particles from ethylcellulose use is made of ethylcellulose having a polymerization degree of 150 to 600, and substitution degree of 2 to 2.6 (proportion of ethoxy groups 44 to 50%), for example Ethylcellulose 45 m (Serva Feinbiochemica GMBH and Co., BRD).

The composition is prepared and used as described in Example 5. The result is similar to those obtained in Examples 1 to 9 and 15.

A similar result is obtained by using catheters having larger inner diameters.

TABLE 1

Influence of local ischemia on tumor growth and survival period of animals

| | | Changes in the tumor volume (cu. cm) depending on the time of tumor transplantation | | |
|---|---|---|---|---|
| No | Type of action | 5 days | 7 days | 9 days |
| 1 | Ligation of vessels | 11.5 ± 2.8 | 20.3 ± 3.7 | 26.4 ± 4.1 |
| 2 | Reference group | 11.3 ± 3.1 | 29.8 ± 4.4 | 56.4 ± 5.7 |

TABLE 1 (cont)

| | Changes in the tumor volume (cu. cm) depending on the time of tumor transplantation | | | | Lifetime |
|---|---|---|---|---|---|
| No. | 11 days | 13 days | 15 days | 17 days | (days) |
| 1 | 42.3 ± 6.5 | 66.7 ± 8.3 | 82.7 ± 9.5 | 104.6 ± 11.7 | 21.4 ± 2.7 |
| 2 | 78.2 ± 3.1 | 101.5 ± 10.4 | — | — | 16.7 ± 2.4 |

TABLE 2

Influence of cyclophosphane introduced during local ischemia on the tumor growth and survival period of animals

| | | Change of tumor volume (cu. cm) depending on the time of tumor transplantation | | |
|---|---|---|---|---|
| No. | Type of action | 5 days | 7 days | 9 days |
| 1 | Ligation of vessels cyclophosphane | 12.1 ± 2.9 | 11.6 ± 2.7 | 10.4 ± 2.2 |
| 2 | Infusion of cyclophosphane | 11.4 ± 2.6 | 10.1 ± 2.2 | 8.3 ± 1.9 |
| 3 | Ligation of vessels | 11.7 ± 2.8 | 21.2 ± 3.2 | 27.8 ± 3.7 |
| 4 | Reference group | 11.8 ± 2.7 | 30.4 ± 4.3 | 59.6 ± 6.2 |

| | Change of tumor volume (cu. cm) depending on the time of tumor transplantation | | | | Lifetime |
|---|---|---|---|---|---|
| No. | 11 days | 13 days | 15 days | 17 days | (days) |
| 1 | 10.6 ± 2.6 | 11.2 ± 2.7 | 18.7 ± 3.9 | 29.7 ± 4.3 | 31.6 ± 4.2 |
| 2 | 5.3 ± 1.6 | 11.7 ± 2.2 | 27.4 ± 2.8 | 42.4 ± 5.1 | 26.3 ± 3.8 |
| 3 | 40.4 ± 4.8 | 65.3 ± 7.6 | 87.2 ± 9.4 | 102.7 ± 13.1 | 22.1 ± 2.9 |

TABLE 2-continued

Influence of cyclophosphane introduced during local ischemia on the tumor growth and survival period of animals

| 4 | 81.4 ± 9.5 | 108.7 ± 12.3 | | 15.8 ± 2.8 |
|---|---|---|---|---|

TABLE 3

Influence of infusion of the proposed composition containing polyehyleneoxide and cyclophosphane on tumor growth and lifetime of animals

| No. | Type of action | Changes in tumor volume (cu. cm) depending on the time of tumor transplantation | | | |
|---|---|---|---|---|---|
| | | 5 days | 7 days | 9 days | 11 days |
| 1. | Infusion of proposed composition + cyclophospane | 12.2 ± 3.1 | 31.4 ± 4.8 | 45.2 ± 5.8 | 43.1 ± 5.2 |
| 2. | Infusion of proposed composition wiout cyclophosphane | 12.1 ± 3.0 | 30.2 ± 4.5 | 60.9 ± 6.9 | 78.6 ± 8.1 |
| 3 | Infusion of cyclophosphane | 11.4 ± 2.9 | 10.9 ± 2.5 | 9.1 ± 2.1 | 7.5 ± 1.5 |
| 4 | Reference group | 11.8 ± 2.7 | 28.6 ± 3.6 | 55.8 ± 6.4 | 75.1 ± 9.1 |

| No. | Changes in tumor volume (cu. cm) depending on the time of tumor transplantation | | | | Lifetime (days) |
|---|---|---|---|---|---|
| | 13 days | 15 days | 17 days | 19 days | |
| 1 | 39.4 ± 4.1 | 34.1 ± 4.1 | 31.1 ± 3.9 | 40.2 ± 6.1 | 27.1 ± 2.8 |
| 2 | 105.1 ± 14.2 | — | — | — | 15.8 ± 2.1 |
| 3 | 12.7 ± 3.2 | 32.4 ± 4.1 | 56.4 ± 6.6 | 87.4 ± 9.7 | 23.4 ± 2.5 |
| 4 | 101.3 ± 12.6 | — | — | — | 16.1 ± 1.7 |

TABLE 4

Influence of the proposed composition containing polyethyleneoxide and cyclophosphane against the background of local ischemia on tumor growth and lifetime of animals

| No. | Type of action | Changes in tumor volume (cu. cm) depending on time of tumor transplantation | | | |
|---|---|---|---|---|---|
| | | 5 days | 8 days | 11 days | 14 days |
| 1 | Infusion of proposed composition containing cyclophosphane + vessel ligation | 11.9 ± 2.6 | 16.3 ± 3.4 | 23.5 ± 3.7 | 33.8 ± 4.1 |
| 2 | Infusion of proposed composition containing cyclophosphane | 11.3 ± 2.5 | 37.5 ± 4.4 | 47.6 ± 5.1 | 48.6 ± 4.9 |
| 3 | Vessel ligation | 12.2 ± 3.2 | 21.5 ± 3.8 | 27.5 ± 4.2 | 68.1 ± 7.6 |
| 4 | Reference group | 12.5 ± 3.5 | 36.9 ± 4.5 | 78.6 ± 6.7 | 103.1 ± 12.8 |

| No. | Changes in tumor volume (cu. cm) depending on time of tumor transplation | | | Lifetime (days) |
|---|---|---|---|---|
| | 17 days | 20 days | 23 days | |
| 1 | 25.7 ± 3.5 | 17.7 ± 3.1 | 20.9 ± 4.2 | 37.4 ± 4.1 |
| 2 | 34.9 ± 4.6 | 21.5 ± 3.6 | 56.3 ± 6.2 | 29.4 ± 3.4 |
| 3 | 79.4 ± 8.9 | 111.5 ± 14.6 | — | 22.9 ± 3.1 |
| 4 | — | — | — | 17.1 ± 2.1 |

What is claimed is:

1. A method for the embolization of blood vessels comprising infusing a composition comprising, in weight percent, the following ingredients:
   spherical particles of embolizing material selected from the group consisting of acetylcellulose, acetylphtalycellulose, polyvinylacetate, a copolymer of vinylpyrrolidone and methylmethacrylate, of a diameter of 0.2 to 0.3 mm, 0.01–15%;
   polyalkyleneoxide of a molecular weight of 500 to 5,000, 0.01–2%; and the balance fluid medium; through a syringe and a catheter into a blood vessel.

2. A method for the embolization of blood vessels comprising infusing a composition, comprising, in weight percent, spherical particles of embolizing material selected from the group consisting of acetylcellulose, acetylphtalycellulose, polyvinylacetate, and a copolymer of vinylpyrrolidone and methylmethacrylate, of a diameter of from 0.2 to 0.3 mm, from 0.01 to 15%; a polyalkyleneoxide of a molecular weight of from 400 to 200,000, from 0.02 to 0.2%; and the balance fluid medium, through a syringe into a blood vessel, wherein said polyalkyleneoxide is selected from a group consisting of polymethyleneoxide, polyethyleneoxide and polypropyleneoxide.

* * * * *